United States Patent
Keshwani et al.

(10) Patent No.: US 12,159,411 B2
(45) Date of Patent: Dec. 3, 2024

(54) MACHINE LEARNING DEVICE AND METHOD

(71) Applicant: FUJIFILM Corporation, Tokyo (JP)

(72) Inventors: Deepak Keshwani, Tokyo (JP); Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 1076 days.

(21) Appl. No.: 16/996,871

(22) Filed: Aug. 18, 2020

(65) Prior Publication Data

US 2020/0380313 A1    Dec. 3, 2020

Related U.S. Application Data

(63) Continuation of application No. PCT/JP2019/007049, filed on Feb. 25, 2019.

(30) Foreign Application Priority Data

Feb. 28, 2018  (JP) ................................ 2018-035354

(51) Int. Cl.
   *G06N 3/08*     (2023.01)
   *G06F 18/24*   (2023.01)
   (Continued)

(52) U.S. Cl.
   CPC ............... *G06T 7/11* (2017.01); *G06F 18/24* (2023.01); *G06N 3/08* (2013.01); *G06T 7/0012* (2013.01);
   (Continued)

(58) Field of Classification Search
   CPC .................. G06F 18/24; G06T 7/0012; G06T 2207/20084; G06T 2207/30004; G06N 3/08
   See application file for complete search history.

(56) References Cited

U.S. PATENT DOCUMENTS 10,825,168 B2 * 11/2020 Tegzes ..................... G06T 7/11
2015/0161782 A1   6/2015 Mohr et al.
(Continued)

FOREIGN PATENT DOCUMENTS

JP    2015112487    6/2015
JP    2017512091    5/2017
JP    2017182320   10/2017

OTHER PUBLICATIONS

Ye F, Pu J, Wang J, Li Y, Zha H. Glioma grading based on 3D multimodal convolutional neural network and privileged learning. In2017 IEEE International Conference on Bioinformatics and Biomedicine (BIBM) Nov. 13, 2017 (pp. 759-763). IEEE. (Year: 2017).*

Mishra A, Marr D. Apprentice: Using knowledge distillation techniques to improve low-precision network accuracy. arXiv preprint arXiv:1711.05852. Nov. 15, 2017. (Year: 2017).*

(Continued)

*Primary Examiner* — Oluwatosin Alabi
(74) *Attorney, Agent, or Firm* — JCIPRNET

(57) ABSTRACT

Provided is a machine learning device and method that enables machine learning of labeling, in which a plurality of labels are attached to volume data at one effort with excellent accuracy, using training data having label attachment mixed therein.

A probability calculation unit (14) calculates a value (soft label) indicating a likelihood of labeling of a class Ci for each voxel of a second slice image by means of a learned teacher model (13a). A detection unit (15) detects "bronchus" and "blood vessel" for the voxels of the second slice image using a known method, such as a region expansion method and performs labeling of "bronchus" and "blood vessel". A correction probability setting unit (16) replaces the soft label with a hard label of "bronchus" or "blood vessel" detected by the detection unit (15). A distillation unit (17) performs distillation of a student model (18a) from the teacher model (13a) using the soft label after correction by (Continued)

means of the correction probability setting unit (16). With this, the learned student model (18*a*) is obtained.

10 Claims, 3 Drawing Sheets

(51) Int. Cl.
*G06T 7/00* (2017.01)
*G06T 7/11* (2017.01)
*G06V 10/82* (2022.01)

(52) U.S. Cl.
CPC .... *G06V 10/82* (2022.01); *G06T 2207/10081* (2013.01); *G06T 2207/20084* (2013.01)

(56) References Cited

U.S. PATENT DOCUMENTS

| | | | |
|---|---|---|---|
| 2015/0238158 A1 | 8/2015 | Zhou et al. | |
| 2018/0061058 A1* | 3/2018 | Xu | G06N 3/084 |
| 2018/0247715 A1* | 8/2018 | Kumar | G06N 3/045 |
| 2019/0065897 A1* | 2/2019 | Li | G06F 18/2415 |
| 2019/0080455 A1* | 3/2019 | Chen | G06N 3/045 |
| 2020/0320685 A1* | 10/2020 | Anssari Moin | G06T 7/11 |

OTHER PUBLICATIONS

Xiangrong Zhou et al., "Simultaneous Recognition and Segmentation of Multiple Anatomical Structures on CT Images by Using Deep Learning Approach", Medical Imaging Technology, Sep. 2017, Submit with English abstract, pp. 187-193.

Siqi Liu et al., "3D Anisotropic Hybrid Network:Transferring Convolutional Features from 2D Images to 3D Anisotropic Volumes", Computer Vision and Pattern Recognition, Nov. 2017, pp. 1-17.

"Office Action of Japan Counterpart Application", issued on Oct. 25, 2021, with English translation thereof, pp. 1-7.

"International Search Report (Form PCT/ISA/210) of PCT/JP2019/007049," mailed on May 14, 2019, with English translation thereof, pp. 1-4.

"Written Opinion of the International Searching Authority (Form PCT/ISA/237) of PCT/JP2019/007049," mailed on May 14, 2019, with English translation thereof, pp. 1-7.

Geoffrey Hinton, et al., "Distilling the Knowledge in a Neural Network," Mar. 2015, pp. 1-9, available at https://arxiv.org/abs/1503.02531.

Stergios Christodoulidis, "Multisource Transfer Learning With Convolutional Neural Networks for Lung Pattern Analysis," IEEE Journal of Biomedical and Health Informatics, vol. 21, Jan. 2017, pp. 76-84.

\* cited by examiner

MACHINE LEARNING DEVICE AND METHOD

CROSS-REFERENCE TO RELATED APPLICATIONS

The present application is a Continuation of PCT International Application No. PCT/JP2019/007049 filed on Feb. 25, 2019 claiming priority under 35 U.S.C § 119(a) to Japanese Patent Application No. 2018-035354 filed on Feb. 28, 2018. Each of the above applications is hereby expressly incorporated by reference, in its entirety, into the present application.

BACKGROUND OF THE INVENTION

1. Field of the Invention

The present invention relates to a machine learning device and method, and in particular, to a machine learning device and method for constructing a machine learning model that performs classification (segmentation) of a structure of an image.

2. Description of the Related Art

Hitherto, there is a technique, called "distillation", in which, using a learned model that decides to which of a plurality of labels each pixel value belongs for three-dimensional medical image data (volume data), such as a computed tomography (CT) image, makes a learning model with a scale smaller than the learned model perform machine learning. Distillation refers to calculating a probability (a value referred to as a soft target or a soft label) of classification using a softmax function and updating a weight of a neural network of another learning model different from the learned model using the soft target.

SUMMARY OF THE INVENTION

In finding classification of a lung, there are more than 30 image patterns, such as "normal", "reticular", "honeycombing", "ground-glass", "mild Low attenuation area (LAA)", "moderate LAA", "severe LAA", "traction bronchodilatation", and "punctate shadow". In a case where ground truth labels for machine learning of the image patterns are created, it is easy to merely surround a target region with two-dimensional slice images, but it is hard to create a ground truth label with a three-dimensional slice image.

Accordingly, it is considered that a two-dimensional image is input and a neural network is made to perform learning to construct a learning model, and the learning model is applied for each slice of a three-dimensional image. However, in a case where a structure to be classified is a three-dimensional structure, such as a blood vessel or a bronchus, and in a case where a manner that the three-dimensional structure appears varies, the learning model cannot classify the structure with high accuracy. For example, a blood vessel that travels vertically in a slice is classified as a punctate shadow. On the other hand, three-dimensional labeling of a blood vessel or a bronchus is easier than labeling of a disease pattern.

An object of the invention is to provide a machine learning device and method that enables efficient distillation according to a structure to be classified with higher accuracy.

According to a first aspect of the invention, there is provided a machine learning device comprising a probability calculation unit that, by means of a first learned model, which is constructed using a first neural network and is able to perform classification of first volume data, calculates a probability indicating a likelihood of classification of second volume data different from the first volume data, a correction probability setting unit that sets a correction probability obtained by correcting the probability indicating the likelihood of classification of the second volume data, and a machine learning unit that makes a second neural network different from the first neural network perform machine learning for obtaining a second learned model different from the first learned model based on the second volume data and the correction probability.

According to a second aspect of the invention, in the machine learning device, the first volume data is two-dimensional data, and the second volume data is three-dimensional data.

According to a third aspect of the invention, in the machine learning device, the first volume data is a two-dimensional medical tomographic image, and the second volume data is a three-dimensional medical tomographic image including a plurality of two-dimensional medical tomographic images having a slice thickness thinner than the first volume data.

According to a fourth aspect of the invention, in the machine learning device, the first neural network is a two-dimensional convolutional neural network, and the second neural network is a three-dimensional convolutional neural network.

According to a fifth aspect of the invention, in the machine learning device, the first volume data is three-dimensional data, and the second volume data is four-dimensional data.

According to a sixth aspect of the invention, in the machine learning device, the correction probability setting unit sets the correction probability based on at least one result of region extraction obtained from the second volume data through manual or automatic labeling for the probability of classification of the second volume data calculated from the probability calculation unit.

According to a seventh aspect of the invention, in the machine learning device, the correction probability setting unit sets the correction probability based on classification discriminated by a region expansion method.

According to an eighth aspect of the invention, there is provided a machine learning method comprising a step of, by means of a first learned model, which is constructed using a first neural network and is able to perform classification of first volume data, calculating a probability indicating a likelihood of classification of second volume data different from the first volume data, a step of setting a correction probability obtained by correcting the probability indicating the likelihood of classification of the second volume data, and a step of making a second neural network different from the first neural network perform machine learning for obtaining a second learned model different from the first learned model based on the second volume data and the correction probability.

A machine learning program that causes a computer to execute the above-described machine learning method and a machine-learned model that is machine-learned by the machine learning program are also included in the invention. In addition, a non-transitory computer readable recording medium that, in a case where a command stored in the recording medium is read by a computer, causes the computer to execute the above-described machine learning program is also included in the invention.

According to the invention, in a case where a probability (soft label) is corrected by accurate classification (hard label) obtained by a region expansion method or the like of the related art to perform distillation, it is possible to make another model perform learning from a learned model with higher accuracy.

DESCRIPTION OF THE PREFERRED EMBODIMENTS

Figure 1:
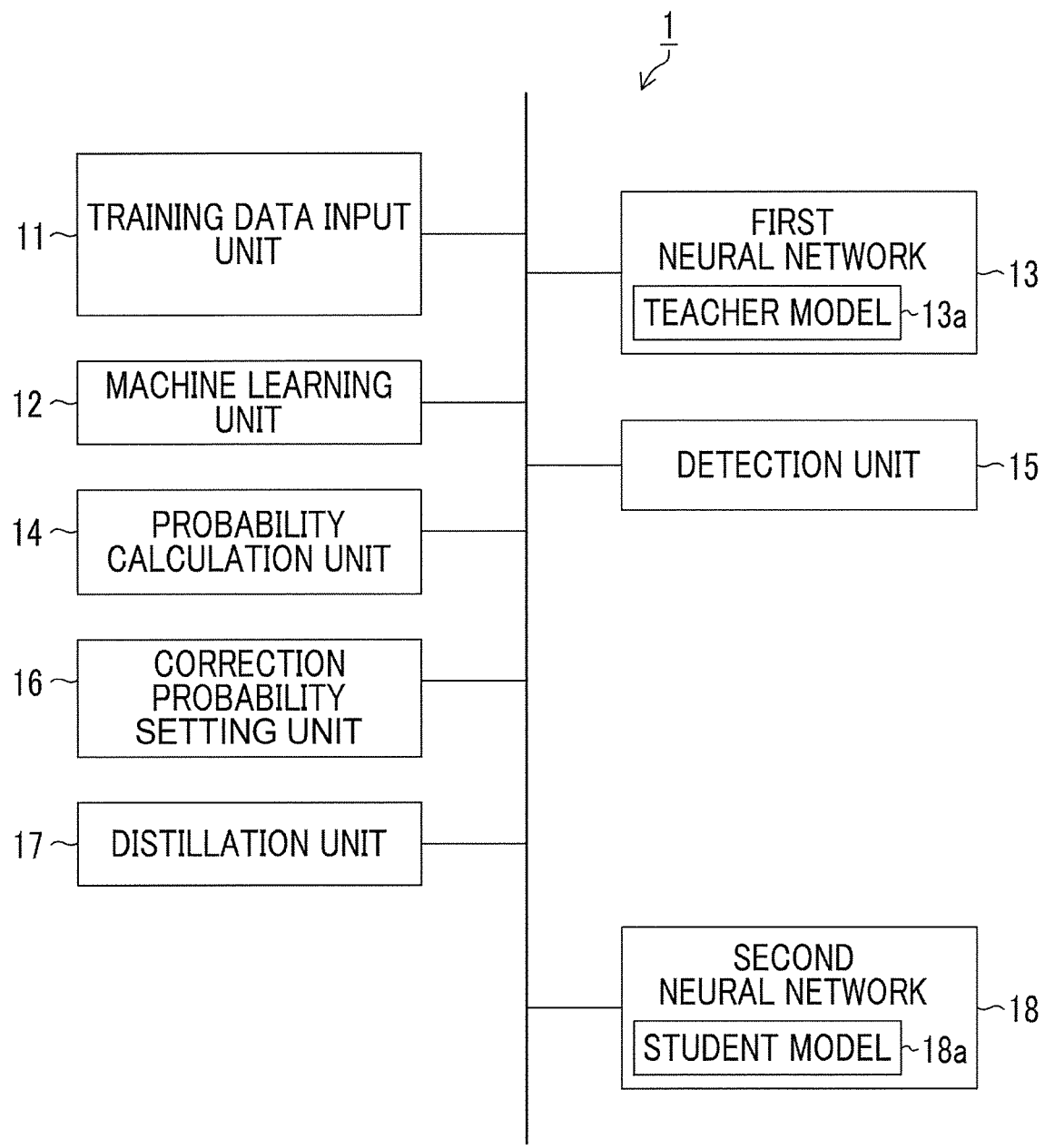
FIG. 1 is a schematic configuration diagram of a machine learning device.

FIG. 1 is a schematic configuration diagram of a machine learning device 1 according to a preferred embodiment of the invention. The machine learning device 1 comprises a training data input unit 11, a machine learning unit 12, a first neural network 13, a probability calculation unit 14, a correction probability setting unit 16, and a second neural network 18.

The training data input unit 11 receives an input of a set (training data) of first volume data having one axial tomographic image (first slice image Ithick) and a ground truth mask in which a physician or the like manually attaches ground truth labels, such as "pulmonary parenchyma", "bronchus", "blood vessel", "tumor", and "others", to respective voxels included in the first volume data and respective pixels in an image are classified into n kinds of anatomical structures (class Ci, $1 \leq i \leq n$).

The first neural network 13 is a two-dimensional convolutional neural network. The machine learning unit 12 makes the first neural network 13 perform machine learning based on training data input from the training data input unit 11 and obtains a learned model (teacher model 13a) that performs labeling of a slice image.

The teacher model 13a obtained through learning of the first neural network 13 performs labeling to voxels of respective slice images (second slice images Ithin-1, Ithin-2, . . . ) of second volume data having a number of axial tomographic images (multi-slice image) input from the training data input unit 11. The multi-slice image may be video having a planar images and an imaging time.

Figure 2:
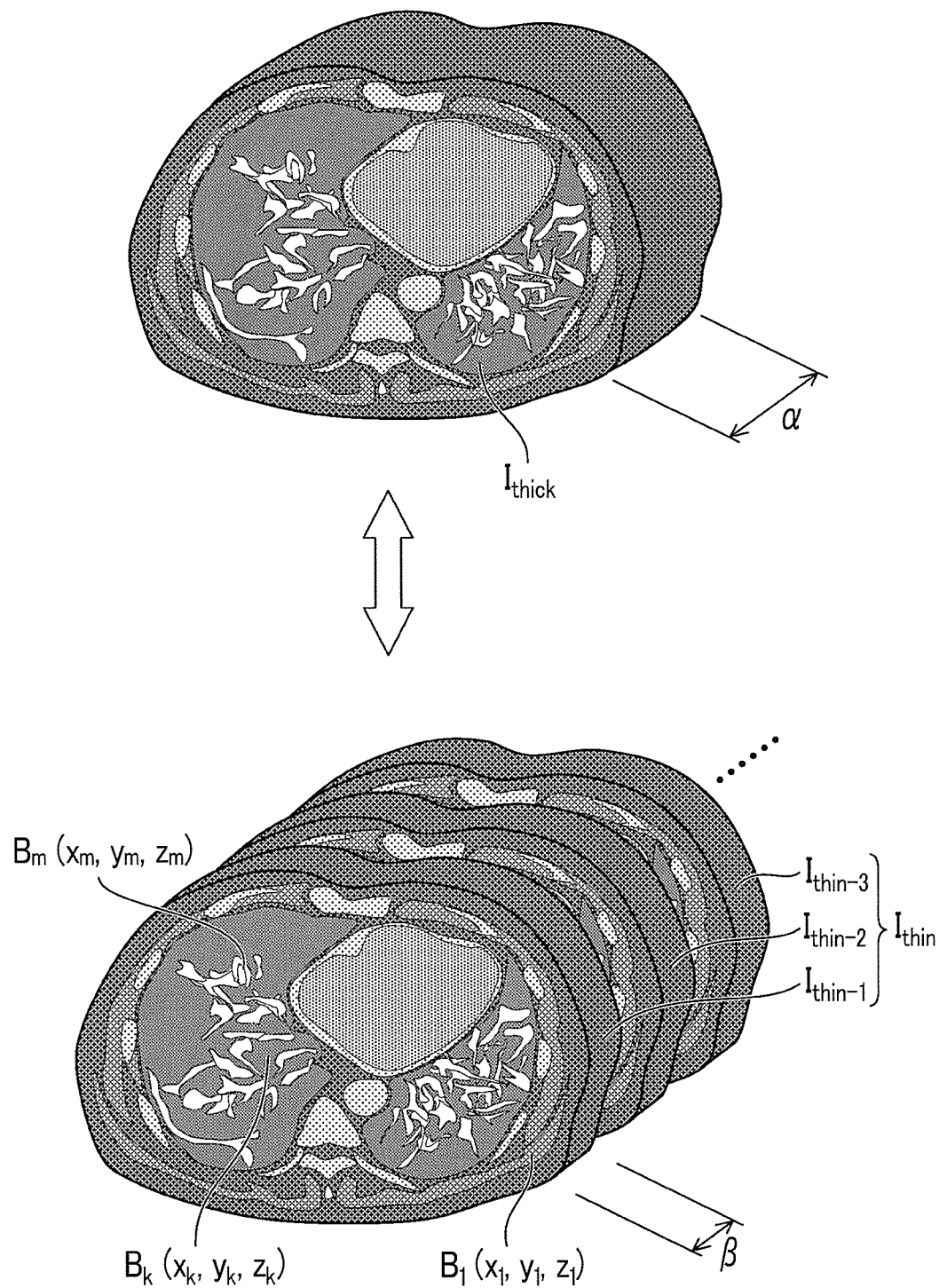
FIG. 2 is a diagram showing an example of a slice image.

As shown in FIG. 2, a slice thickness β of the second slice images Ithin-1, Ithin-2, . . . is thinner than a slice thickness α of the first slice image Ithick of the training data. That is, α>β.

In a case where the slice thickness α of the first slice image Ithick or the slice thickness β of the second slice images Ithin-1, Ithin-2, . . . is negligible, the slice images can be handled as pseudo two-dimensional image data. For this reason, it is possible to perform labeling for each voxel of the first slice image Ithick or the second slice images Ithin-1, Ithin-2, . . . with the first neural network 13. The teacher model 13a is obtained from a set of the first slice image Ithick and the ground truth mask.

The teacher model 13a performs labeling a class Ci, such as pulmonary parenchyma, bronchus, blood vessel, tumor, and others, for each voxel of the second slice images Ithin-1, Ithin-2, . . . .

The probability calculation unit 14 calculates a value pi (soft label) indicating a likelihood of labeling of the class Ci for each voxel of the second slice image by means of the learned teacher model 13a.

As described in Geoffrey Hinton, Oriol Vinyals, Jeff Dean, "Distilling the Knowledge in a Neural Network", the Internet <URL https://arxiv.org/abs/1503.02531>, in a case where a softmax layer of the teacher model 13a is used, a soft label for each voxel of the second slice image, that is, a probability pi with a temperature of each class Ci can be obtained by the following expression (a softmax function with a temperature). vi is a logit. Note that T is normally 1, but the greater the value for T is, the softer an output distribution of each model is.

$$p_i = \frac{\exp\left(\frac{v_i}{T}\right)}{\Sigma_j \exp\left(\frac{v_j}{T}\right)}$$

For example, assuming that a subscript i=1 to 5 of the class Ci corresponds to "pulmonary parenchyma", "bronchus", "blood vessel", "tumor", and "others", a probability pi (B1) with a temperature of each class Ci using the softmax layer of the teacher model 13a for a voxel B1 in coordinates (x1,y1,z1) of the second slice image Ithin-1 is calculated as follows.

$p1(B1)$(=soft label of pulmonary parenchyma for voxel $B1$)=0.8

$p2(B1)$(=soft label of bronchus for voxel $B1$)=0.03

$p3(B1)$(=soft label of blood vessel for voxel $B1$)=0.05

$p4(B1)$(=soft label of tumor for voxel $B1$)=0.05

$p5(B1)$(=soft label of others for voxel $B1$)=0.07

Note that the accuracy of detection of an anatomical structure extending in an axial direction, such as a bronchus or a blood vessel, by means of the teacher model 13a cannot be considered to be high. This is because α>β, and there is a possibility that information indicating the feature of the bronchus or the blood vessel in the first slice image is lost in the individual second slice image.

The detection unit 15 detects "bronchus" and "blood vessel" for the voxels of the second slice image using a known method, such as a region expansion method, and performs labeling of "bronchus" and "blood vessel". Labeling of "bronchus" and "blood vessel" is a hard label, a probabilistic likelihood of which is 0 or 1. Alternatively, the detection unit 15 may detect labeling of "bronchus" and "blood vessel" for the voxels of the second slice image based on a manual operation of a physician or the like, thereby giving the hard label, the probabilistic likelihood of which is 0 or 1, to each voxel.

For example, in regard to the detection of "bronchus" using the region expansion method, a method that extracts a continuous region having a pixel value corresponding to an air region in the bronchus (in particular, a method that connects adjacent pixels having approximate pixel values to such an extent as to satisfy a predetermined condition) is exemplified. Since the connection of the pixels is performed even in the axial direction, it is possible to extract a bronchus with comparatively high accuracy from the second slice image.

For example, in regard to the detection of "blood vessel", other than the region expansion method, a method that extracts a region, which is likely to be a blood vessel, with a line filter based on a Hessian matrix or the like and connects the extracted region to an unclassified blood vessel region to expand the unclassified blood vessel region is exemplified.

As other detection methods of "bronchus" and "blood vessel", there are known methods, such as a graph cut method and a level set method.

Note that the detection unit 15 may detect an anatomical structure other than "bronchus" and "blood vessel" from the second slice image using a known method. For example, the detection unit 15 may detect a cardiac lumen region using the region expansion method. The detection unit 15 can detect an anatomical structure, such as "bronchus" or "blood vessel", from the second slice image by means of automatic detection, a manual operation, or a combination thereof.

The correction probability setting unit 16 replaces the soft label of the voxel with the hard label of "bronchus" or "blood vessel" detected by the detection unit 15 in the voxel of the second slice image.

For example, in a case where the hard label "1" of "bronchus" is given for a voxel Bk in coordinates (xk,yk,zk) different from the coordinates (x1,y1,z1) of the second slice image Ithin-1 by the detection unit 15, the soft label of the voxel Bk is rewritten as follows.

$p1(Bk)$(=soft label of pulmonary parenchyma for voxel $Bk$)=0.8→0.0

$p2(Bk)$(=soft label of bronchus for voxel $Bk$)=0.35→1

$p3(Bk)$(=soft label of blood vessel for voxel $Bk$)=0.05→0.0

$p4(Bk)$(=soft label of tumor for voxel $Bk$)=0.0

$p5(Bk)$(=soft label of tumor for voxel $Bk$)=0.0

Alternatively, in a case where the hard label "1" of "blood vessel" is given for a voxel Bm in coordinates (xm,ym,zm) different from the coordinates (x1,y1,z1) and (xk,yk,zk) by the detection unit 15, the soft label of the voxel Bm is rewritten as follows.

$p1(Bm)$(=soft label of pulmonary parenchyma for voxel $Bm$)=0.2→0.0

$p2(Bm)$(=soft label of bronchus for voxel $Bm$)=0.1→0.0

$p3(Bm)$(=soft label of blood vessel for voxel $Bm$)=0.4→1

$p4(Bm)$(=soft label of tumor for voxel $Bm$)=0.1→0.0

$p5(Bm)$(=soft label of tumor for voxel $Bm$)=0.3→0.0

In regard to a voxel where the hard label of "bronchus" or "blood vessel" is not detected by the detection unit 15, the soft label is not rewritten.

The second neural network 18 is a three-dimensional convolutional neural network.

The distillation unit 17 performs distillation of an unlearned student model 18a of the second neural network 18 from the teacher model 13a using the soft label after correction by means of the correction probability setting unit 16 and the uncorrected soft label, thereby obtaining a learned student model 18a. Distillation should follow the method described in Geoffrey Hinton, Oriol Vinyals, Jeff Dean, "Distilling the Knowledge in a Neural Network", the Internet <URL https://arxiv.org/abs/1503.02531>.

That is, the probability calculation unit 14 first calculates a value qi (soft label) indicating a likelihood of labeling of the class Ci for each voxel of the second slice image by means of the student model 18a.

As described in Geoffrey Hinton, Oriol Vinyals, Jeff Dean, "Distilling the Knowledge in a Neural Network", the Internet <URL https://arxiv.org/abs/1503.02531>, the soft label for each voxel of the second slice image, that is, a probability qi with a temperature of each class Ci is obtained using a softmax layer of the second neural network 18. qi is obtained by the following expression (a softmax function with a temperature). zi is a logit.

$$q_i = \frac{\exp\left(\frac{z_i}{T}\right)}{\Sigma_j \exp\left(\frac{Z_j}{T}\right)}$$

Distillation by means of the distillation unit 17 minimizes a gradient of a cross entropy C for zi.

$$\partial C/\partial z_i \approx 1/NT^2 (z_i - v_i)$$

An output distribution of qi of the student model 18a becomes close to an output distribution of pi of the teacher model 13a by means of distillation. Note that T is normally 1, but the greater the value for T is, the softer an output distribution of each model is.

Typically, although distillation distills the learned knowledge of a large and complicated neural network (teacher) and uses the learned knowledge for learning of a small and lightweight model (student), whereby it is possible to achieve application to the student model 18a of the three-dimensional neural network from the teacher model 13a of the two-dimensional neural network with the use of Expressions 1 and 2 described above.

Figure 3:
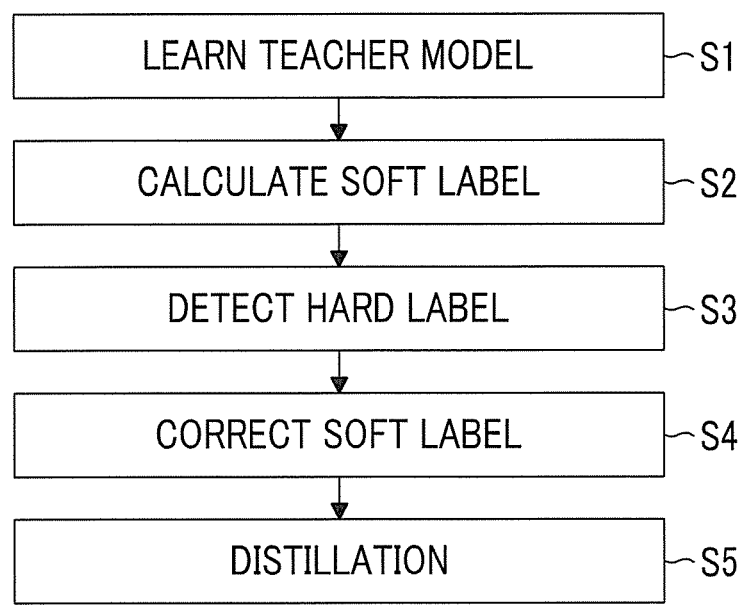
FIG. 3 is a flowchart of machine learning processing.

FIG. 3 is a flowchart of machine learning processing that is executed by the machine learning device 1.

In S1 (teacher model learning step), the machine learning unit 12 makes the first neural network 13 perform machine learning based on training data having the set of the first slice image and the ground truth mask input from the training data input unit 11, thereby obtaining the learned teacher model 13a that can perform labeling to the second slice image.

In S2 (soft label calculation step), the probability calculation unit 14 calculates the soft label pi indicating the likelihood of labeling of the class Ci for each voxel of the second slice image by the learned teacher model 13a.

In S3 (hard label detection step), the detection unit 15 detects "bronchus" and "blood vessel" using a known method, such as the region expansion method, for the voxel of the second slice image, and performs labeling of "bronchus" and "blood vessel".

In S4 (soft label correction step), the correction probability setting unit 16 corrects the soft label pi with the hard label of "bronchus" or "blood vessel" detected by the detection unit 15.

In S5 (distillation step), the distillation unit 17 performs distillation of the student model 18a from the teacher model 13a using the soft label after correction by means of the correction probability setting unit 16 and the uncorrected soft label. With this, the learned student model 18a is obtained from the teacher model 13a.

Since the teacher model 13a is a model learned with the first slice image, the likelihoods of the soft labels of "bronchus" and "blood vessel" of the second slice images obtained by the teacher model 13a are not considered to be high in accuracy. In contrast, the hard labels of "bronchus"

and "blood vessel" obtained in the detection unit 15 can be accurately extracted using the region expansion method or the like of the related art. With the use of the characteristics, in a case where the soft labels of "bronchus" and "blood vessel" of the second slice images are corrected with the hard labels and distillation is performed, it is possible to make the student model 18a perform learning from the teacher model 13a with higher accuracy.

In the above-description, although the first neural network 13 is a two-dimensional convolutional neural network, the second neural network 18 is a three-dimensional convolutional neural network, the first volume data is a pseudo two-dimensional image, and the second volume data is a three-dimensional image, the dimensions of the first neural network 13 and the second neural network 18 are not limited to the dimensions described above.

For example, the first neural network 13 may be a three-dimensional neural network, the second neural network 18 may be a two-dimensional neural network, the first volume data may be a pseudo three-dimensional image, and the second volume data may be a two-dimensional image. The pseudo three-dimensional image may be one frame of video having a planar image and an imaging time.

Alternatively, the first neural network 13 may be a three-dimensional neural network, the second neural network 18 may be a four-dimensional neural network, the first volume data may be a three-dimensional image, and the second volume data may be a four-dimensional image. The four-dimensional image may be video having a stereoscopic image and an imaging time.

The teacher model 13a and the student model 18a may be models constructed using different neural networks, and the dimensions of the respective neural networks may be the same or may be different. For example, the teacher model 13a and the student model 18a may be constructed using different two-dimensional neural networks, three-dimensional neural networks, or four-dimensional neural networks.

EXPLANATION OF REFERENCES

11: training data input unit
12: machine learning unit
13: first neural network
13a: teacher model
14: probability calculation unit
15: detection unit
16: correction probability setting unit
17: distillation unit
18: second neural network
18a: student model

What is claimed is:

1. A machine learning device comprising:
   a non-transitory storage medium configured to store at least a first volume data, a second volume data, and a first neural network and
   a processor coupled to the non-transitory storage medium and configured to:
      obtain the first volume data and a ground truth label manually attached to corresponding voxels in the first volume data,
      derive a first learned model from the first volume data and the ground truth label to train the first neural network to perform classifications on a first slice image of the first volume data, wherein the first neural network is a two-dimensional convolution neural network (CNN),
      perform a classification of a second slice image of the second volume data with the first learned model, wherein the slice thickness of the second slice image is thinner than the slice thickness of the first slice image,
      calculate a first probability indicating a likelihood of the classification of the second slice image of the second volume data which has more information than the first volume data and attach a soft label associated with the first probability to the classification,
      perform a detection of a predetermined structure corresponding to the classification from the second volume data,
      set a correction probability by correcting the first probability and associate the classification with a hard label indicating the likelihood of the classification of the second volume data, wherein the correction probability corresponding to the predetermined structure is either 1 or 0, and
      derive a second learned model by performing a distillation from the first learned model to an unlearned model of a second neural network based on the second volume data and the correction probability.

2. The machine learning device according to claim 1, wherein the first volume data is two-dimensional data, and the second volume data is three-dimensional data.

3. The machine learning device according to claim 2, wherein the first volume data is a two-dimensional medical tomographic image, and
   the second volume data is a three-dimensional medical tomographic image including a plurality of two-dimensional medical tomographic images having a slice thickness thinner than the first volume data.

4. The machine learning device according to claim 2, wherein the second neural network is a three-dimensional convolutional neural network.

5. The machine learning device according to claim 1, wherein the first volume data is three-dimensional data, and the second volume data is four-dimensional data.

6. The machine learning device according to claim 1, wherein the processor is configured to set the correction probability based on at least one result of region extraction obtained from the second volume data by manual or automatic labeling for the first probability of classification of the second volume data calculated by the processor.

7. The machine learning device according to claim 6, wherein the processor is configured to set the correction probability based on classification discriminated by a region expansion method.

8. A machine learning method used by a machine learning device having a non-transitory storage medium configured to store at least a first volume data, a second volume data, and a first neural network and a processor coupled to the non-transitory storage medium, the method comprising:
   obtaining the first volume data and a ground truth label manually attached to corresponding voxels in the first volume data,
   deriving, by the processor, a first learned model from the first volume data and the ground truth label to train the first neural network to perform classifications on a first slice image of the first volume data, wherein the first neural network is a two-dimensional convolution neural network (CNN),
   performing, by the processor, a classification of a second slice image of the second volume data with the first learned model, wherein the slice thickness of the second slice image is thinner than the slice thickness of the first slice image, calculating, by the processor, a first probability indicating a likelihood of the second slice image of the classification of the second volume data which has more information than the first volume data and attach a soft label associated with the first probability to the classification, performing, by the processor, a detection of a predetermined structure corresponding to the classification from the second volume data, setting, by the processor, a correction probability by correcting the first probability and associate the classification with a hard label indicating the likelihood of the classification of the second volume data, wherein the correction probability corresponding to the predetermined structure is either 1 or 0, and deriving, by the processor, a second learned model by performing a distillation from the first learned model to an unlearned model of a second neural network based on the second volume data and the correction probability.

9. A machine-learned model that is machine-learned by the machine learning method according to claim 8.

10. A non-transitory computer readable recording medium which records commands thereon that, when read by a computer, cause the computer to execute the machine learning method according to claim 8.

* * * * *